(12) United States Patent
Dampney et al.

(10) Patent No.: US 7,004,957 B1
(45) Date of Patent: Feb. 28, 2006

(54) ACTUATING AND LOCKING MECHANISM FOR A SURGICAL TOOL

(75) Inventors: Ian Trevor Dampney, London (GB); John Ewant Alfred Wickham, London (GB)

(73) Assignee: Syclix Limited, Pinner (GB)

( * ) Notice: Subject to any disclaimer, the term of this patent is extended or adjusted under 35 U.S.C. 154(b) by 0 days.

(21) Appl. No.: 09/890,581

(22) PCT Filed: Feb. 4, 2000

(86) PCT No.: PCT/GB00/00325

§ 371 (c)(1),
(2), (4) Date: Mar. 8, 2002

(87) PCT Pub. No.: WO00/45718

PCT Pub. Date: Aug. 10, 2000

(30) Foreign Application Priority Data

Feb. 5, 1999 (GB) .................................... 9902647

(51) Int. Cl.
*A61B 17/50* (2006.01)

(52) U.S. Cl. ...................................... 606/211; 604/159

(58) Field of Classification Search ............... 606/170, 606/127, 108, 192, 198, 99, 100, 104; 604/159, 604/198, 22; 81/487, 489, 491
See application file for complete search history.

(56) References Cited

U.S. PATENT DOCUMENTS

| | | | | |
|---|---|---|---|---|
| 2,510,198 A | | 6/1950 | Tesmer | |
| 3,982,544 A | * | 9/1976 | Dyck | 604/271 |
| 4,258,716 A | * | 3/1981 | Sutherland | 606/170 |
| 4,996,974 A | * | 3/1991 | Ciarlei | 600/149 |
| 5,158,086 A | * | 10/1992 | Brown et al. | 600/459 |
| 5,195,507 A | * | 3/1993 | Bilweis | 600/204 |
| 5,250,056 A | | 10/1993 | Hasson | |
| 5,282,817 A | | 2/1994 | Hoogeboom et al. | |
| 5,346,504 A | * | 9/1994 | Ortiz et al. | 606/192 |
| 5,355,871 A | * | 10/1994 | Hurley et al. | 606/170 |
| 5,474,571 A | * | 12/1995 | Lang | 606/205 |
| 5,741,270 A | | 4/1998 | Hansen et al. | |
| 5,752,972 A | | 5/1998 | Hoogeboom | |
| 6,030,406 A | * | 2/2000 | Davis et al. | 606/198 |

FOREIGN PATENT DOCUMENTS

WO        WO 96/00030        1/1996

OTHER PUBLICATIONS

Copy of International Search Report.

* cited by examiner

*Primary Examiner*—Julian W. Woo
*Assistant Examiner*—Victor X. Nguyen
(74) *Attorney, Agent, or Firm*—Blank Rome LLP

(57) ABSTRACT

An actuating mechanism for actuating a surgical tool of a surgical instrument including an actuating device having an actuator surface. The actuating device is operable by applying a force to substantially any part of the actuator surface for placing the actuating device in an actuated position from a rest position for actuating a surgical tool. The actuator surface comprises a radially collapsible cage having a plurality of interdigitating actuating pads. Each pad is movable in a radial direction.

25 Claims, 5 Drawing Sheets

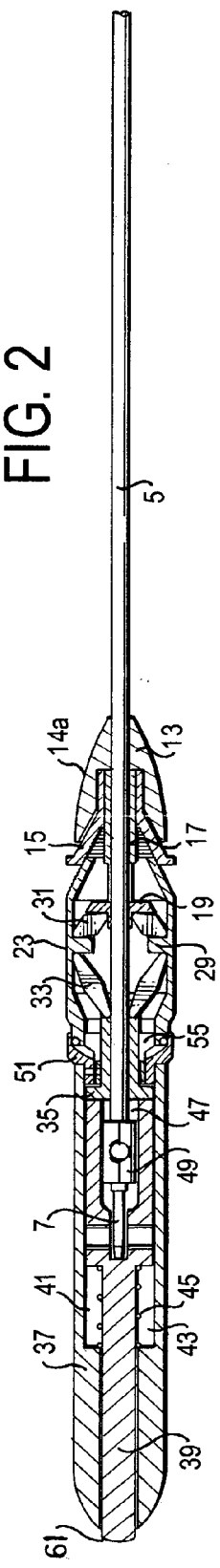
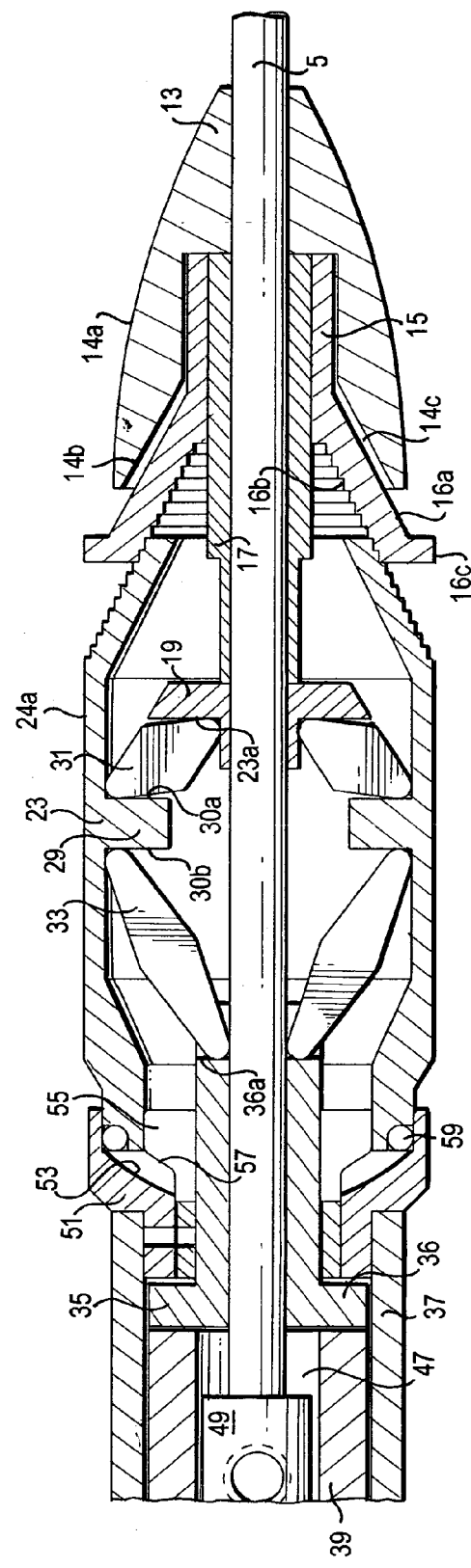
FIG. 2
FIG. 3

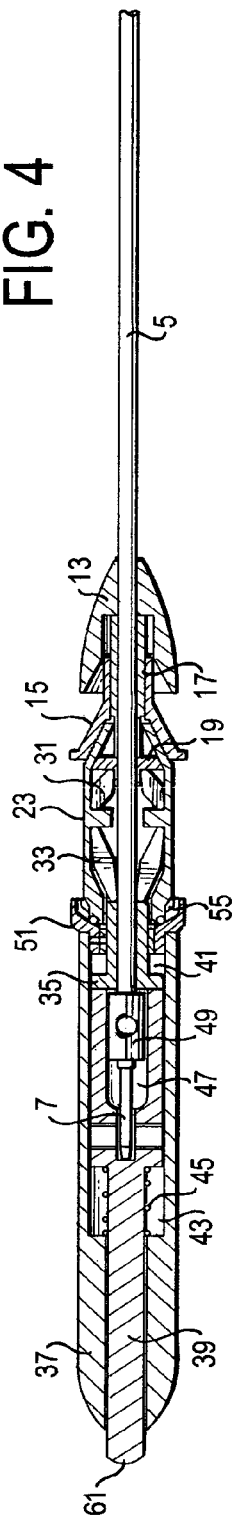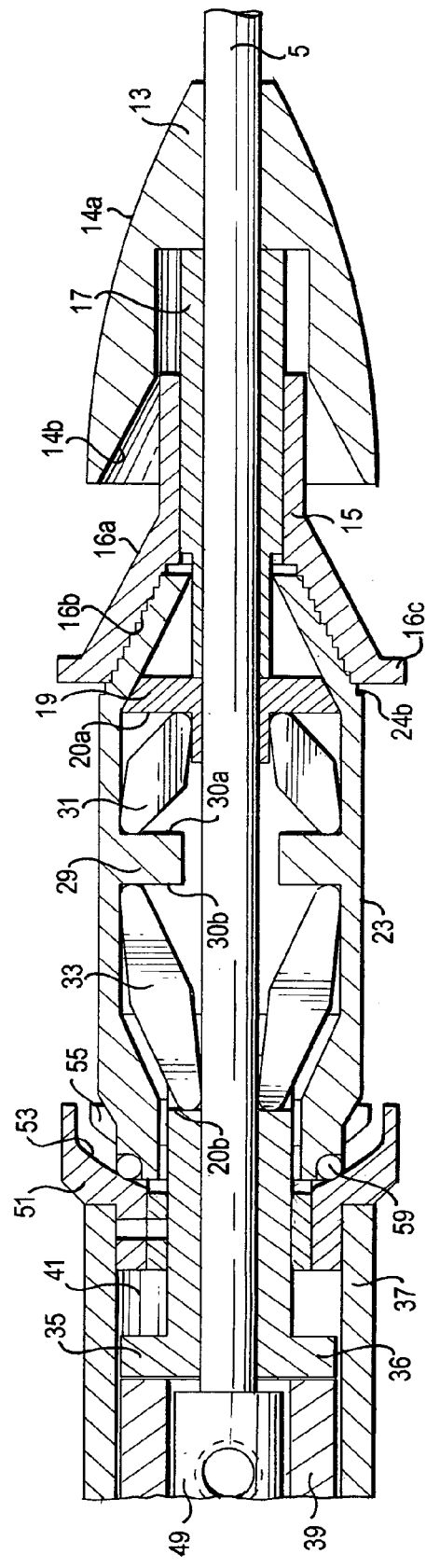

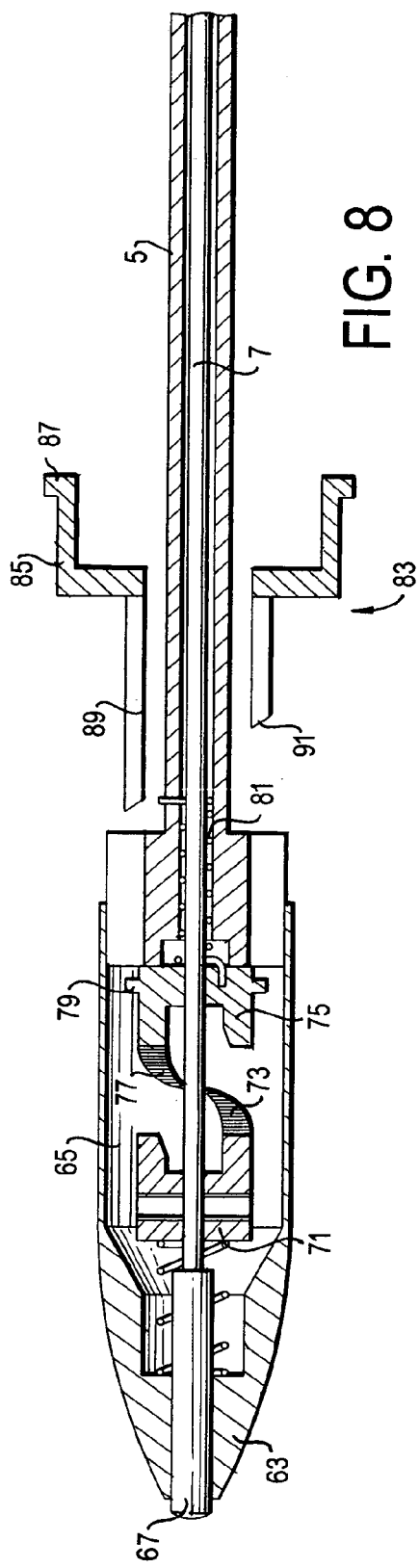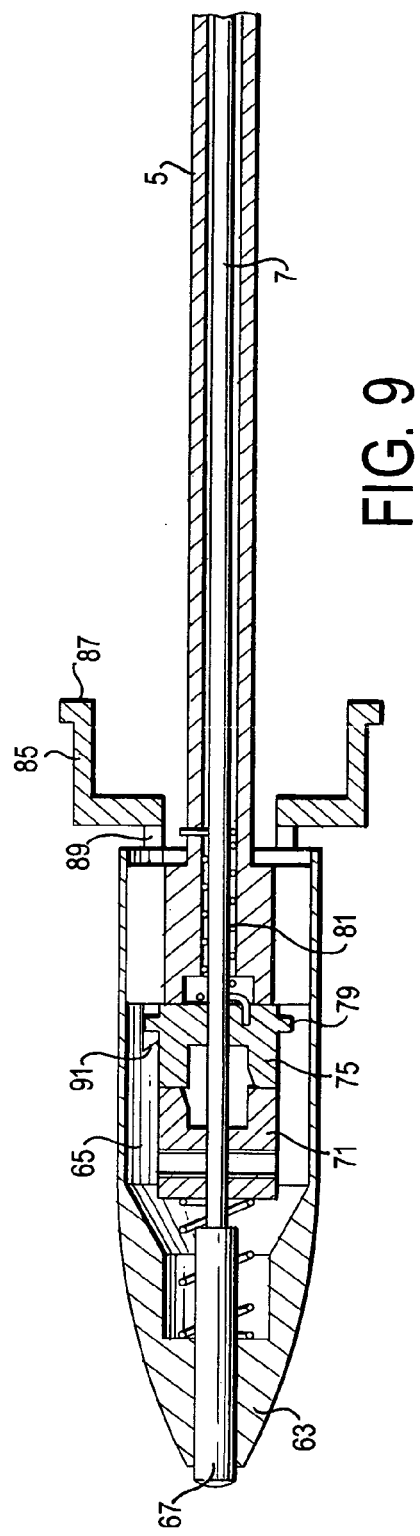

ACTUATING AND LOCKING MECHANISM FOR A SURGICAL TOOL

FIELD OF THE INVENTION

The present invention relates to an actuating mechanism for actuating a surgical tool of a surgical instrument. It also relates to a locking mechanism for locking a surgical tool of a surgical instrument.

Minimal invasive surgery, known as key hole surgery, has become increasingly popular. The surgery involves making only a small incision in the patient and inserting a specifically designed implement through the incision. The implement comprises a miniaturised surgical implement such as forceps, clamps, scissors or diathermy hooks at the end of a long shaft with a handle attached to the other end for actuating the implement. The implement is inserted so that the handle is outside of the patient and, therefore the surgeon can operate on the patient through the small incision with minimal invasion. This type of surgery minimises the trauma experienced by the patient, reducing post-operation complications and improving patient's recovery time.

Conventionally, the handle of the implement is a scissors-type handle. It has been found that such a handle does not provide steady control and it is difficult to rotate the implement and therefore, it can not easily be manipulated by one hand.

This has been solved by providing a surgical instrument which is held in a pen-like grip. The handle of the instrument extends rearwardly between the surgeon's thumb and forefinger. The instrument can be rotated between the thumb and forefinger so that it can be manipulated easily by one hand and actuation of the tool at the other end of the instrument can easily be achieved by simply applying a force at a point along the handle between the thumb and forefinger.

A known type of instrument, which is held in a pen-like grip, is disclosed by WO 96/24298. The surgical instrument comprises a bulbous portion in which a plurality of discrete flexible actuating members are arranged around the circumference of the bulbous portion of the handle so that the user can depress any one of the actuator elements arranged around the circumference of the handle to actuate the surgical tool. However, it has been found that the bulbous portion of the handle is uncomfortable and the movement of the actuator elements to actuate the surgical tool requires a certain pressure to be applied to them to bring about actuation. This pressure has to be sufficient to overcome the resilience of the actuator members. This pressure can, in certain circumstances, be excessive making fine control of the surgical tool difficult. A further disadvantage is that the flexible actuating members tend to distort under pressure, so that the force output and movement of the instrument is irregular and unpredictable.

BACKGROUND OF THE INVENTION

Furthermore, this known type of instrument has a mechanism of locking the tool in its actuated position. However, such a mechanism does not provide intermediatary positioning of the tool as is sometimes required.

SUMMARY OF THE INVENTION

An object of the present invention is to provide a surgical tool in which the above disadvantages are overcome.

According to one aspect of the present invention, there is provided an actuating mechanism for actuating a surgical tool of a surgical instrument comprising an actuating device having an actuator surface whereby the actuating device is operable by applying a force to substantially any part of the actuator surface to place the actuating device in an actuated position from a rest position for actuating a surgical tool, wherein the actuator surface comprises a radially collapsible cage, having a plurality of interengaging actuating pads, each pad being movable in a radial direction.

In providing such an actuator surface, the handle of the surgical instrument is more like a pen which makes it more comfortable when held between the thumb and forefinger. The surface can be cylindrical and as such can be made to move an equidistance at any axial point along the surface. The shape of the actuator members of the prior art, however, means that the central portion has to be moved a greater distance by virtue of the bulbous shape and therefore the actuation of the device of the prior art is less sensitive. The pressure required to actuate the surgical tool by the actuator of the present invention is less and hence fine control of the surgical tool can be achieved.

Each pad may have an inwardly extending groove and the actuating device further comprising a plurality of radially extending guides, each guide engaging a respective inwardly extending groove of each pad so that each pad moves inwardly and outwardly in a radial direction. Preferably, the surgical tool is actuated by inward radial movement of the cage. The actuating mechanism may further comprise means for allowing each pad to move in unison. This may be in the form of a locking collar.

The rib cage provides an actuator surface which is more sensitive since its movement is not dependent on the resiliency of the actuator elements and therefore only a slight pressure needs to be applied to bring about actuation. The rib cage also provides a cylindrical surface which is more comfortable for the user and which is insensitive to radial orientation. Furthermore, the rib cage has a sufficiently rigid structure to resist both circumferential and axial distortion during use.

In a further preferred embodiment, the actuating mechanism comprises a locking mechanism for locking the actuating device in its actuated position. The actuating device may have a plurality of actuated positions and the locking mechanism is adapted to lock the actuating mechanism in any one of its actuated positions. The locking mechanism may further comprise release means for unlocking the actuating device from its actuated position into its rest position.

The actuating mechanism may further comprise override means for unlocking the actuating device from its actuated position to its rest position in an emergency such as in the event of the effector becoming jammed by tissue in its closed position. The override means may be in the form of a manually operated push button.

In yet a further preferred embodiment, the actuating mechanism comprises biasing means for biasing the actuating device in its unactuated position. The biasing means may comprise a resilient means such as a compression spring.

According to a further aspect of the present invention, there is provided a locking mechanism for locking a surgical tool of a surgical instrument in its actuated position comprising interengaging means having a plurality of settings to lock the surgical tool in any one of a plurality of actuated positions, the interengaging means comprising latching means and actuator means wherein the latching means comprises a first stepped surface and the actuator means comprises a second stepped surface, any one of the steps of the second stepped surface of the actuator means interengaging any one of the steps of the first stepped surface of the latching means to lock the actuator means in any one of a plurality of actuated positions, wherein the axial depth of each step of the second stepped surface of the actuator means is greater than the axial depth of each step of the first stepped surface of the latching means. In a preferred arrangement the axial depth of a step of the stepped surface of the latching means may be an exact multiple of the axial depth of a step of the stepped surface of the actuator means. The stepped surface or surfaces may be conical or spiral, having planar, cylindrical, pyramidal or polygonal shaped steps.

The locking mechanism therefore provides means for setting the surgical tool in a number of different positions so that the tool can be locked at different degrees of actuation which provides accurate control of the instrument during surgery.

In a further preferred embodiment, the locking mechanism comprises release means for releasing the interengaging means form its locked position into an unlocked position.

The locking mechanism may further comprise override means for unlocking the interengaging means in an emergency such as the tool becoming jammed in its closed position and operation of the actuator is sufficient to release it. The override means may be a manually operated push button. The interengaging means may be biased in its unlocked position so that on release of the latching and actuator means, the surgical tool returns to its rest position.

According to a further aspect of the present invention, there is provided a surgical instrument comprising a handle, an elongate shaft extending from the handle and a surgical tool mounted on the shaft at a location remote from the handle, the instrument further comprising an actuating mechanism described above.

The actuating mechanism of the surgical instrument may be integral with the handle. Further, the diameter of the cylindrical surface defined by the actuator surface of the actuating mechanism may be approximately equal to the diameter of the handle.

The elongate shaft preferably comprises an actuator rod slideably mounted within an outer tube, the surgical tool being actuated by respective longitudinal movement between the actuator rod or the outer tube. The actuating device comprises means for translating the radial movement of the actuator surface into the longitudinal movement for actuating the surgical tool. The translation means may be in the form of a plurality of radius arms which extend in an axial direction upon application of the force to a part of the actuator surface.

According to a further aspect of the present invention, there is provided a surgical instrument comprising a handle, an elongate shaft extending from the handle and an effector mounted on the shaft at a location remote from the handle, the instrument further comprising a locking mechanism described above.

In a preferred embodiment, the elongate shaft comprises an actuator rod slideably mounted within an outer tube, the effector being actuated by respective longitudinal movement between the actuator rod or the outer tube, wherein the locking mechanism locks the actuator rod with respect to the outer tube in a plurality of longitudinal positions.

Preferably, the handle is elongate to enable it to be held in a pen-like grip. The surgical tool may comprise miniaturised forceps, clamps, scissors or diathermy books.

BRIEF DESCRIPTION OF THE DRAWINGS

The embodiments of the present invention will now be described with reference to the accompanying drawings, in which:

FIG. 2 is a sectional view of the surgical instrument shown in FIG. 1 in the open position;

FIG. 3 is a sectional view of the actuating mechanism in the open position;

FIG. 4 is a sectional view of the surgical instrument of the present invention in the fully closed position;

FIG. 5 is a sectional view of the actuating mechanism of a present invention in the fully closed position;

FIG. 8 shows an alternative locking mechanism of the surgical instrument according to the present invention in its locked position; and FIG. 9 shows the alternative locking arrangement of FIG. 8 in its locked position.

DETAILED DESCRIPTION OF THE PREFERRED EMBODIMENT

Figure 1:
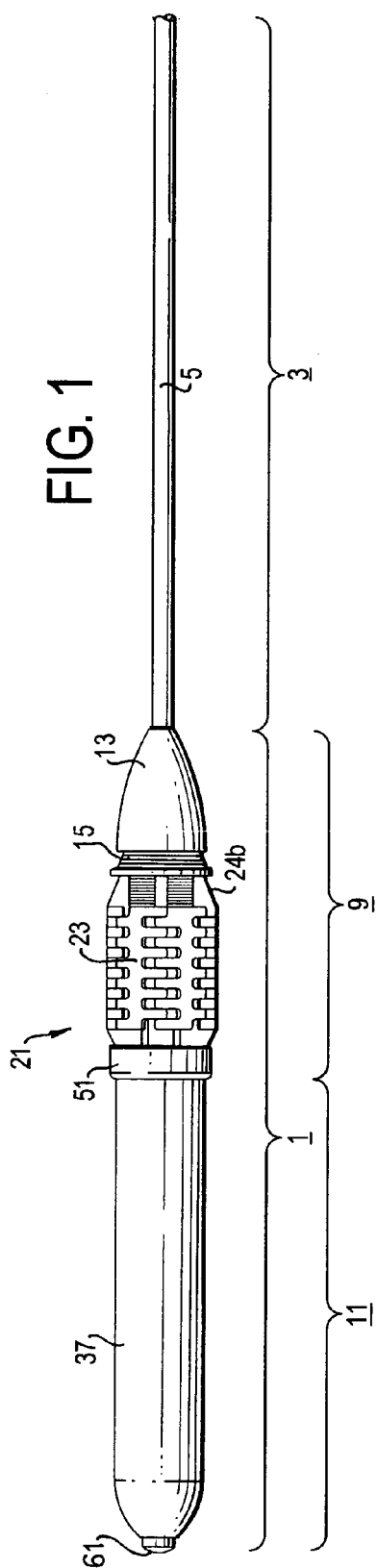
FIG. 1 is a side elevation of the surgical instrument according to an embodiment of the present invention in the open position.
Figure 6:
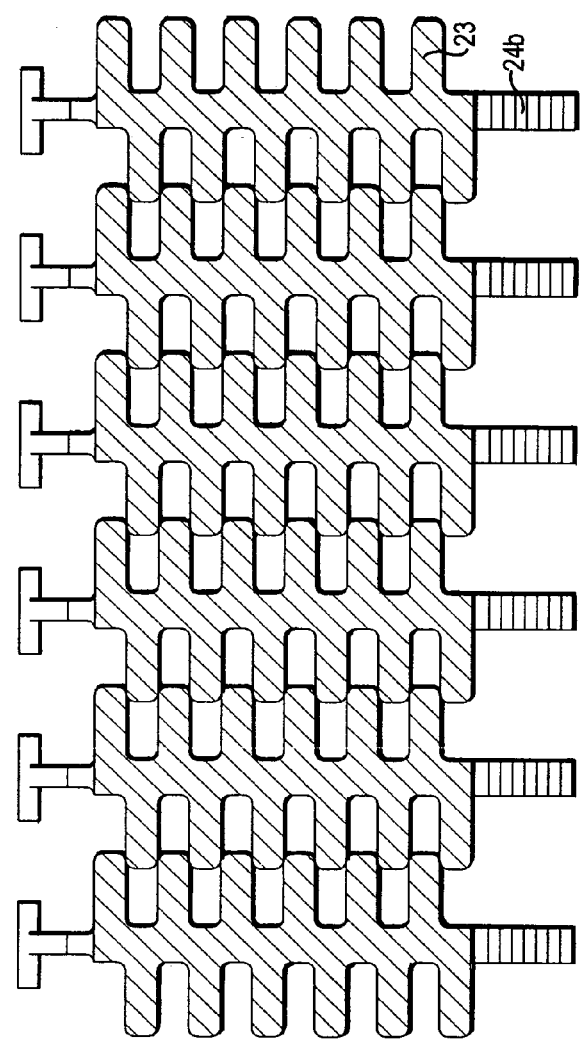
FIG. 6 shows the rib cage of the actuating mechanism of the surgical instrument of the present invention unfolded.

An embodiment of the present invention will now be described with reference to FIGS. 1 to 7b. The surgical instrument comprises an elongate handle 1 having a shaft 3 extending from one end thereof. A surgical tool or effector (not shown) is mounted at the distal end of the shaft 3. The shaft 3 is of a conventional construction and comprises a hollow outer tube 5 in which is slideably mounted an actuator rod 7. The surgical tool or effector, for example forceps, is actuated by the reciprocal movement of the actuator rod 7 within the outer tube 5.

The elongate handle 1 comprises an actuator portion 9 which, in use, is grasped between the thumb and forefinger and middle finger in a pen-like grip with the end portion 11 of the handle extending rearwardly between the thumb and forefinger. The actuator 9 comprises a nose portion 13, which has an outer wall 14a which is curved and tapers outwardly towards the end portion 11 of the handle. The nose portion 13 is fixed to the proximal end of the outer tube 5 of the shaft 3. The nose portion 13 has a blind-ended bore 14c coaxial to the longitudinal axis of the shaft 3. The inner wall 14b of the bore 14c tapers inwardly at a steeper angle than the taper of the outer wall 14a and then extends parallel to the longitudinal axis of the shaft 3 and handle 1 forming a cylindrical portion.

A latch 15 is slideably mounted within the bore 14c of the nose portion 13. The latch 15 has an outer wall 16a which is generally cylindrical at one end, the diameter of which is slightly less than the diameter of the cylindrical portion of the bore 14c of the nose portion 13 so that there is a slight gap between the inner wall 14b of the bore 14c and the outer wall 16a of the latch 15. The outer wall 16a of the latch 15 then tapers outwardly from the cylindrical part of the latch 15 at the same angle as the inner wall 14b of the nose portion 13 such that the gap between the inner wall 14b of the nose portion 13 and the outer wall 16*a* of the latch 15 is maintained. The inner wall 16*b* of the latch 15 generally follows the shape of the outer wall 16*a*. The tapered portion of the inner wall 16*b* of the latch 15 has a plurality of fine cylindrical steps. The latch 15 extends rearwardly out of the nose portion 13 and has an outwardly extending flange 16*c* at the distal end thereof. The flange 16*c* extends outwardly beyond the outer wall 14*a* of the nose portion 13.

A cylindrical spacer 17 is provided along the cylindrical portion of the inner wall 16*b* of the latch 15. The spacer 17 is fixedly attached to the base of the bore 14*c* of the nose portion 13 and extends towards the end portion 11 of the handle beyond the distal end of the latch 15. The spacer 17 is stepped. The latch 15 is therefore sandwiched between the inner wall 14*b* of the nose portion 13 and the spacer 17 and is slideable therebetween. At the distal end of the spacer, there is located a plurality of radially extending finger pad guides 19. These are more clearly shown in FIGS. 7*a* and 7*b*. The diagrams show six finger pad guides, which are equi-spaced around the circumference of the outer tube 5 of the shaft 3. Of course, the number of finger pad guides can be varied as required. The finger pad guides 19 extend radially outwardly to slideably engage an inner groove 27 (described below) of a respective finger pad of the actuator 9.

The actuator portion 9 further comprises a rib cage 21, which consists of a plurality of interleaving or interdigitating finger pads 23. The outer surface 24*a* of the finger pads is curved so that when the finger pads 23 are linked together, they provide a substantially cylindrical surface around the shaft 3. The distal end of each finger pad 23 tapers inwardly at the same angle as the inner wall 16*b* of the latch 15. The outer surface 24*b* of the tapered portion is stepped. The axial depth of the steps of the finger pads 23 are greater than the axial depth of the steps of the latch 15. Any one step of the stepped surface 24*b* of each finger pad 23 interengages any one of the steps of the inner stepped surface 16*b* of the latch 15. Each finger pad 23 further comprises an inwardly extending groove 27, which slideably engages a respective finger pad guide 19. At the midpoint of each finger pad 23, there is provided an inwardly extending protrusion 29 against which rests a plurality of radius arms 31, 33. The first radius arm 31 extends inwardly in a forward direction to rest against the forward edge 30*a* of the protrusion 29 of each finger pad 23 and the rearward edge 20*a* of its respective finger pad guide 19. The second radius arm 33 extends inwardly and rearwardly from the rearward edge 30*b* of the protrusion 29 of each finger pad 23 to rest against the forward edge 36*a* of a drive bush 35. The distal end of each finger pad 23 also tapers inwardly.

The end portion 11 of the handle 1 comprises a generally cylindrical body 37 in which is slideably fitted a thrust yoke 39. The body 37 has a stepped, inner bore 41 so that the inner diameter of the bore 41 of the body 37 increases towards the forward end of the body 37. The thrust yoke 39 is correspondingly stepped to conform to the shape of the bore 41 of the body 37. The shape of the thrust yoke 39 is such that a gap 43 is formed between the bore 41 of the body 37 and the thrust yoke 39. A compression spring 45 is located within the gap 43. The distal end of the thrust yoke 39 has a blind-ended bore 47 in which the actuator rod 7 of the shaft 3 is fixedly attached at one end thereof. The outer tube 5 has a mount 49. The outer tube 5 and mount 49 are slideable with respect to the actuator rod 7 and the bore 47 of the thrust yoke 39.

A generally cylindrical drive bush 35 rests against the forward end of the thrust yoke 39 and is slideable with respect to the outer tube 5 of the shaft 3 and the body 37. The drive bush 35 has an outwardly extending flange 36. An outer guide 51 is fixedly mounted to the forward end of the body 37 to rest against the flange 36 of the bush 35. The outer guide 51 has an inner cam surface 53. An inner guide 55 is fixedly attached within the outer guide 51 having an outer cam surface 55. The inner cam surface 53 of the outer guide 51 and the outer cam surface 57 of the inner guide 55 have a gap therebetween in which a straight T bar or ring 59 fixedly attached to the rearward tapered edge of each finger pad 23 is slideably engaged. The distal end of the thrust yoke 39 extends slightly from the distal end of the body 37 to form an override button 61.

The rib cage 21, in use, is covered with a rubber boot, not shown, to form a sealed unit so that the parts of the actuator portion 9 of the handle 1 is protected from the outside environment.

Figure 7A:
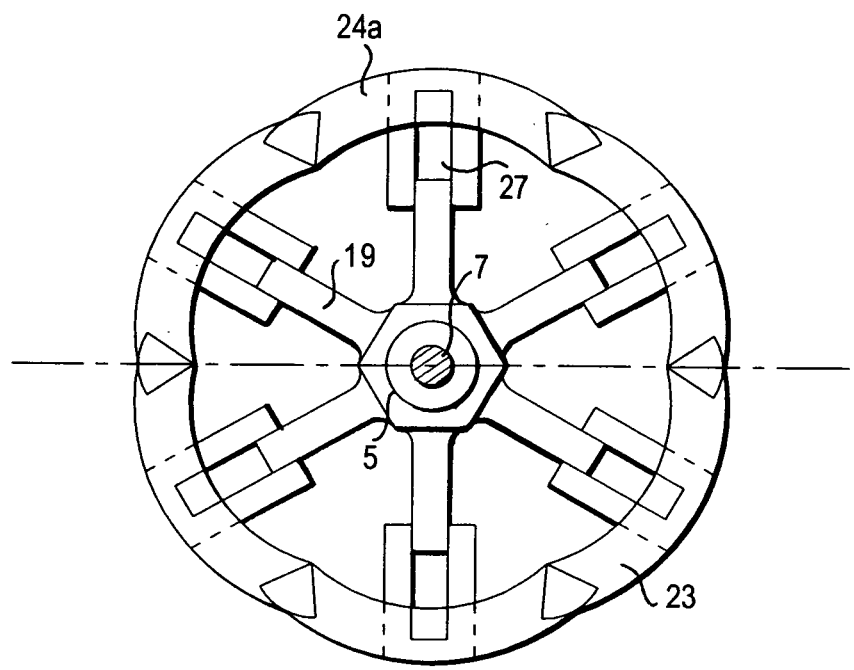
FIG. 7a shows a sectional view taken along the line 7—7 of FIG. 3 of the rib cage of the actuating mechanism of the present invention.
Figure 7B:
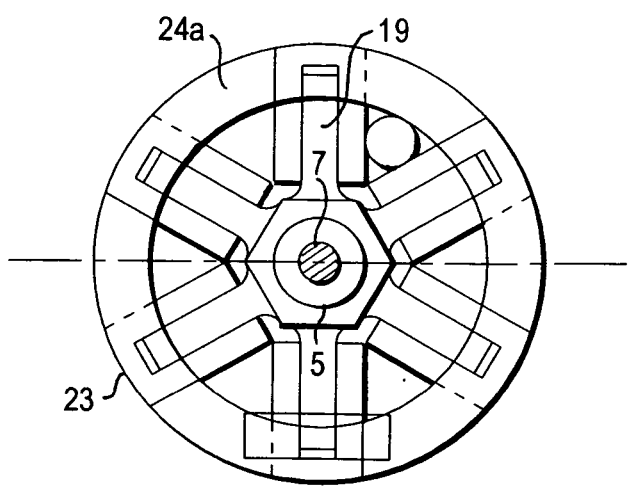
FIG. 7b shows a sectional view taken along the line 7—7 of FIG. 5 of the rib cage of the actuating mechanism of the present invention.

To actuate the tool, the rib cage 21 is compressed inwardly between the thumb and forefinger of the user from its open position, shown in FIGS. 2 and 3, into its closed position as shown in FIGS. 4 and 5. As a result of the interengaging arrangement of the finger pads 23, the rib cage 21 moves synchronously under compression and maintains its cylindrical shape. Compression of the rib cage 21 causes the radius arms 31 and 33 to slide the drive bush 35 and thus the thrust yoke 39 rearwardly. Hence the actuator rod 7 slides rearwardly with respect to the outer tube 5 of the shaft 3 against the bias of the compression spring. On compression of the rib cage 21 the inner groove of each finger pad 23 slides down its respective finger pad guide 19 as shown in FIG. 7*b* and the distal end of each finger pad 23 moves inwardly and due to the stepped surfaces, the latch 15 slides rearwardly up the stepped surface of each finger pad 23 by action of the user's finger or by virtue of a spring and latches at a point along the stepped surface of each finger pad 23 to lock the implement in its actuated position. Since a plurality of steps are provided on each surface, the actuator rod 7 can be locked at a plurality of different longitudinal positions.

To release the surgical tool the latch 15 is moved axially in a forward direction by the user pressing his forefinger against the flange 16*c* of the latch 15. Each finger pad 23 is then released from the latch 15 and is free to move outwardly to its open, unlocked position along the cam surfaces of the inner and outer guides by the compression spring pushing against the thrust yoke 39. As a result the actuator rod 7 slides with respect to the outer tube 5 and hence release the tool at the end of the shaft 3. To help release the engaged step of the finger pads 23 from the latch 15, the rib cage 21 can be compressed slightly.

In the event that the effector or tool becomes jammed and can not be released by normal action of the device, the effector or tool can be actuated by depression of the override button 61. The tool can then be released by manually pushing override button 61 to slide the thrust yoke 39 with respect to the body 37 which forces the actuator rod 7 to slide with respect to the outer tube 5 irrespective of the locking mechanism.

An alternative locking mechanism is shown in FIGS. 8 and 9. The figures illustrate the locking mechanism only, the actuator is not shown. The tool is actuated by sliding the actuator rod 7 with respect to the outer tube 5. It may be utilised in conjunction with the actuator described above or any other suitable actuator.

The handle 1 of the implement houses the actuator (not shown) and locking mechanism. The handle 1 comprises a body 63 having a stepped, inner bore 65. The actuator rod 7 extends through the bore 65 and has an enlarged portion 67 at the distal end thereof. The enlarged portion 67 extends slightly out of the inner bore 65 of the body 63.

The locking mechanism is housed within the enlarged portion of the bore 65 of the body 63. It comprises an upper portion 71, which is fixedly attached to the actuator rod 7 toward the distal end thereof. The upper portion 71 of the lock has a generally cylindrical body with a central bore through which the actuator rod 7 passes. The forward end of the upper portion 71 of the lock comprises a stepped, spiral surface 73. A locking ring 75 is attached to the distal end of the outer tube 5 so that the locking ring 75 can rotate about its axis with respect to the outer tube 5. The locking ring 75 has a complementary stepped spiral surface 77 facing the stepped spiral 73 of the upper portion 71. The locking ring 75 has a pair of diametrically opposing, outwardly extending projections 79. A torsion spring 81 is fixedly attached to one end of the locking ring 75 and the other to the outer tube 5 of the shaft 3 to bias the locking ring rotationally on the axis of the shaft 3.

The locking mechanism also comprises a release ring 83. The release ring 83 is slideable with respect to the shaft 3 and body 63 of the handle 1. The release ring 83 comprises an outer ring portion 85, which has a diameter greater than the diameter of the body of the handle 1. The forward end of the ring portion 85 extends outwardly to a flange 87. The release ring 83 further comprises an inner ring portion 89, which has a diameter less than the diameter of the bore of the body. The proximal end of the inner ring portion 89 provides a spiral cam surface 91.

The locking mechanism operates to lock the actuator rod 7 in a predetermined position with respect to the outer tube 5 by engagement of the complementary stepped surfaces 73, 77 of the upper portion 71 and the locking ring 75. To actuate the tool (mechanism not shown), the actuator rod 7 is caused to slide in a rearward direction with respect to the outer tube 5. As a result the upper portion 71 moves rearwardly with the actuator rod 7. This releases the engagement of the steps and the locking ring 75 can rotate about its axis by virtue of the torsion spring so that the spiral surfaces 73, 77 of the upper portion 71 and the locking ring 75 remain in contact. The inner ring portion 89 of the release ring 83 slides into the bore 65 of the body 63 until the cam surface 91 of the inner ring portion 89 rests on one of the projections 79. To release the actuator rod 7, the outer ring portion 85 is forced to slide axially in a forward direction by the user between their thumb and forefinger. Due to the cam surface 91 running against the projections 79, the locking ring is caused to rotate against the bias of the torsion spring. This causes the locking ring to be released and allows the upper portion 71 to move axially in a forward direction as the stepped surface 73 follows that of the locking ring 75, hence unlocking the device.

The locking mechanism described above and that of the first embodiment can be utilised in conjunction with any known type of actuating mechanism. The stepped surfaces of the locking mechanisms enable the surgical tool to be held in a plurality of settings. Further the actuating mechanism described above can be incorporated with any known type of locking mechanism.

In the light of this disclosure, modifications of the described embodiments as well as other embodiments, all within the scope of the appended claims, will now become apparent to a person skilled in the art.

What is claimed is:

1. An actuating mechanism for actuating a surgical tool of a surgical instrument comprising an actuating device having an actuator surface whereby the actuating device is operable by applying a force to substantially any part of the actuator surface for placing the actuating device in an actuated position from a rest position for actuating a surgical tool, wherein the actuator surface comprises a radially collapsible cage having a plurality of interdigitating actuating pads, each pad being movable in a radial direction.

2. An actuating mechanism according to claim 1, wherein each pad has an inwardly extending groove and the actuating device further comprises a plurality of radially extending guides, each guide engaging a respective inwardly extending groove of each pad so that each pad is capable of inward and outward movement in a radial direction.

3. An actuating mechanism according to claim 1, wherein the cage is adapted such at inward radial movement of the cage causes the actuating device to be placed into its actuated position.

4. An actuating mechanism according claim 1, wherein the actuating mechanism further comprises a locking mechanism for locking the actuating device in its actuated position.

5. An actuating mechanism according to claim 4, wherein the actuating device has a plurality of actuated positions and the locking mechanism is adapted to lock the actuating device in any one of its actuated positions.

6. An actuating mechanism according to claim 4, wherein the locking mechanism further comprises release means for unlocking the actuating device from its actuated positions into its rest position.

7. An actuating mechanism according to claim 4, wherein the actuating mechanism further comprises override means for returning the actuating device from its actuated position to its rest position in the event of the surgical tool becoming jammed.

8. An actuating mechanism according to claim 1, wherein the actuating mechanism further comprises biasing means for biasing the actuating device in its rest position.

9. An actuating mechanism according to claim 8, wherein the biasing means comprises a compression spring.

10. A surgical instrument comprising an handle, an elongate shaft extending from the handle and a surgical tool mounted on the shaft at a location remote from the handle, the instrument further comprising an actuating mechanism according to claim 1.

11. A surgical instruction according to claim 10, wherein the actuating mechanism is integral with the handle.

12. A surgical instrument according to claim 11, wherein the diameter of the cylindrical surface defined by the actuator surface of the actuating device is approximately equal to the diameter of the handle.

13. A surgical instrument according to claim 10, wherein the elongate shaft comprises an actuator rod slideably mounted, within an outer tube, the actuating device actuating the surgical tool by respective longitudinal movement between the actuator rod and the outer tube.

14. A surgical instrument according to claim 13, wherein the actuating device further comprises means for translating the radial movement of the actuator surface into longitudinal movement for actuating the surgical tool.

15. A surgical instrument according to claim 14, wherein the translation means comprises a plurality of radius arms which extend in an axial direction upon application of the force to a circumferential part of the actuator surface.

16. A surgical instrument according to claim 10, wherein the handle is elongate to enable it to be held in a pen-like grip.

17. A surgical instrument according to claim 11, wherein the surgical tool comprises miniaturized forceps, clamps, scissors or diathermy hooks.

18. A locking mechanism for locking a surgical tool of a surgical instrument in its actuated position comprising interengaging means having a plurality of settings to lock the surgical tool in any one of a plurality of actuated positions, the interengaging means comprising latching means and actuator means wherein the latching means comprises a first stepped surface and the actuator means comprises, a second stepped surface, any one of the steps of the second stepped surface of the actuator means interengaging any one of the steps of the first stepped surface of the latching means to lock the actuator means in any one of a plurality of actuated positions, wherein the axial depth of each step of the second stepped surface of the actuator means is greater than the axial depth of each step of the first stepped surface of the latching means.

19. A locking mechanism according to claim 18, wherein the stepped surface or surfaces are conical.

20. A locking mechanism according to claim 18, wherein the stepped surface or surfaces are spiral.

21. A locking mechanism according to claim 18, wherein the locking mechanism further comprises release means for releasing the interengaging means form its locked position into an unlocked position.

22. A locking mechanism according to claim 21, wherein the locking mechanism further comprises biasing means for biasing the interengaging means in its unlocked position.

23. A surgical instrument comprising a handle, an elongate shaft extending from the handle and a surgical tool mounted on the shaft at a location remote from the handle, the instrument further comprising a locking mechanism according to claim 11.

24. A surgical instrument according to claim 23, wherein the elongate shaft comprises an actuator rod slideably mounted within an outer tube, the surgical tool being actuated by respective longitudinal movement between the actuator rod and the outer tube.

25. A surgical instrument according to claim 24, wherein the locking mechanism locks the actuator rod with respect to the outer tube in a plurality of longitudinal positions.

* * * * *